United States Patent
Basler et al.

(10) Patent No.: US 6,394,880 B1
(45) Date of Patent: May 28, 2002

(54) DEVICE AND METHOD FOR PRODUCTION OF MEDICAL FITTINGS

(75) Inventors: Franz Basler, Laudenbach; Stefan Hehn, Bensheim; Bernd Rothenberger, Gernsbach, all of (DE)

(73) Assignee: Sirona Dental Systems GmbH, Bensheim (DE)

( * ) Notice: Subject to any disclaimer, the term of this patent is extended or adjusted under 35 U.S.C. 154(b) by 29 days.

(21) Appl. No.: 09/596,082

(22) Filed: Jun. 16, 2000

(30) Foreign Application Priority Data

Jun. 18, 1999 (DE) .......................... 199 28 002

(51) Int. Cl.[7] .............................................. B24B 51/00
(52) U.S. Cl. ............................................ 451/28; 451/5
(58) Field of Search ................................ 451/28, 41, 5, 451/57, 56; 125/11.02

(56) References Cited

U.S. PATENT DOCUMENTS 5,257,203 A  * 10/1993 Riley et al. ............. 364/474.05
6,133,174 A  * 10/2000 Brodkin et al. ................. 501/6

* cited by examiner

Primary Examiner—Robert A. Rose
(74) Attorney, Agent, or Firm—Dykema Gossett PLLC

(57) ABSTRACT

A device for production of medical fittings, in particular dental restorations, of simple construction, where it is also to be ensured that the restorations are not destroyed by the machining forces. It is of particular importance that the fittings can be made especially quickly and with precision. To achieve this, a device is proposed with a workpiece 1 which can be moved in the axial direction along a feed axis 3, with a first machining tool 5 on one side of the feed axis 3, and with a second machining tool 15 operating simultaneously on the other side of the workpiece 1, in which device the machining tools 5, 15 are designed as rods which can be set in rotation and have radial and terminal working faces 16, 17, 17', and in which device the machining tools 5, 15, during machining of the workpiece 1, are arranged at approximately the same height relative to the feed axis 3 of the workpiece, so that they work along closely adjacent machining areas 32, 33; 44, 45.

Figure 1:
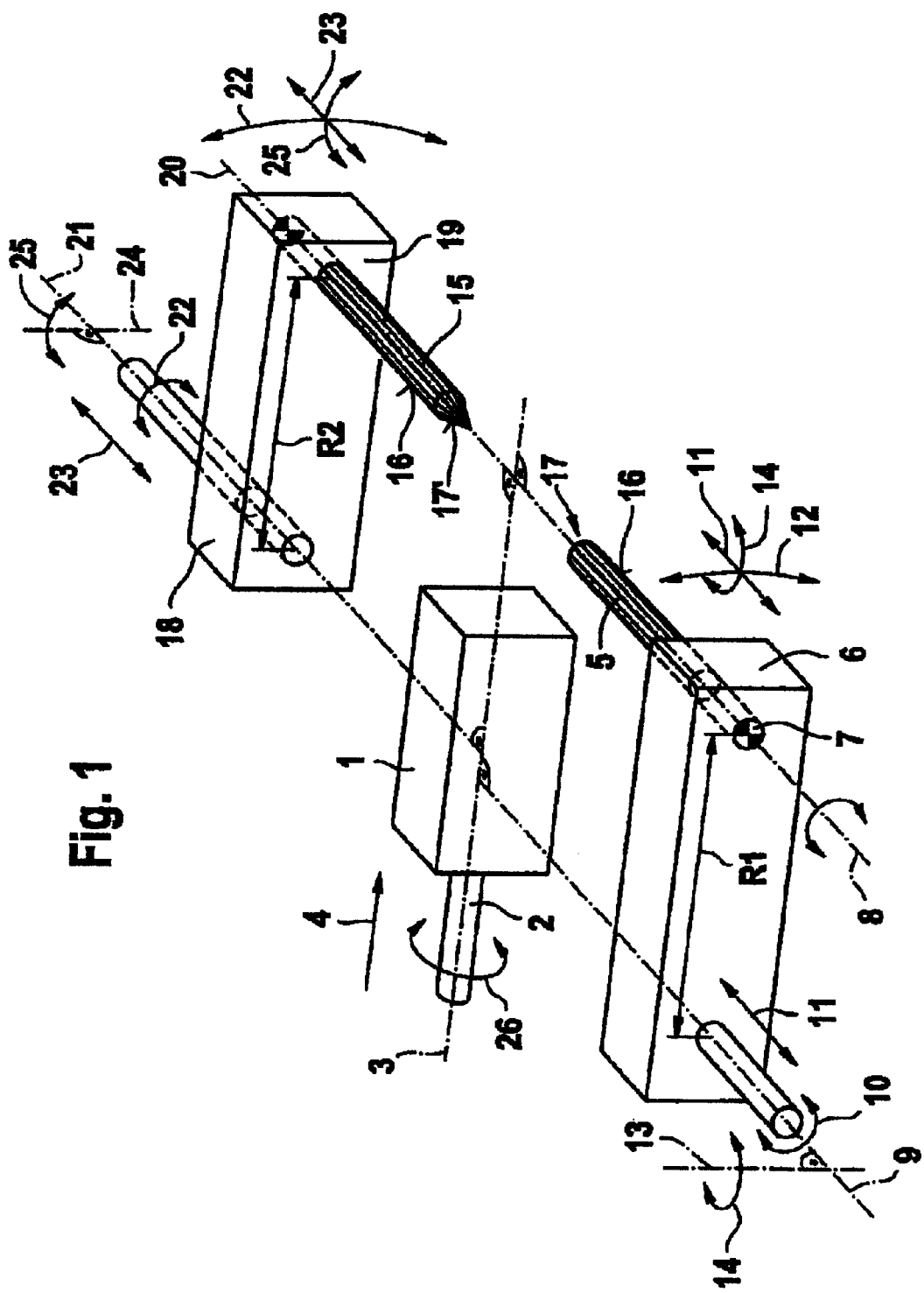

The invention also concerns a method for operating this device.

35 Claims, 4 Drawing Sheets

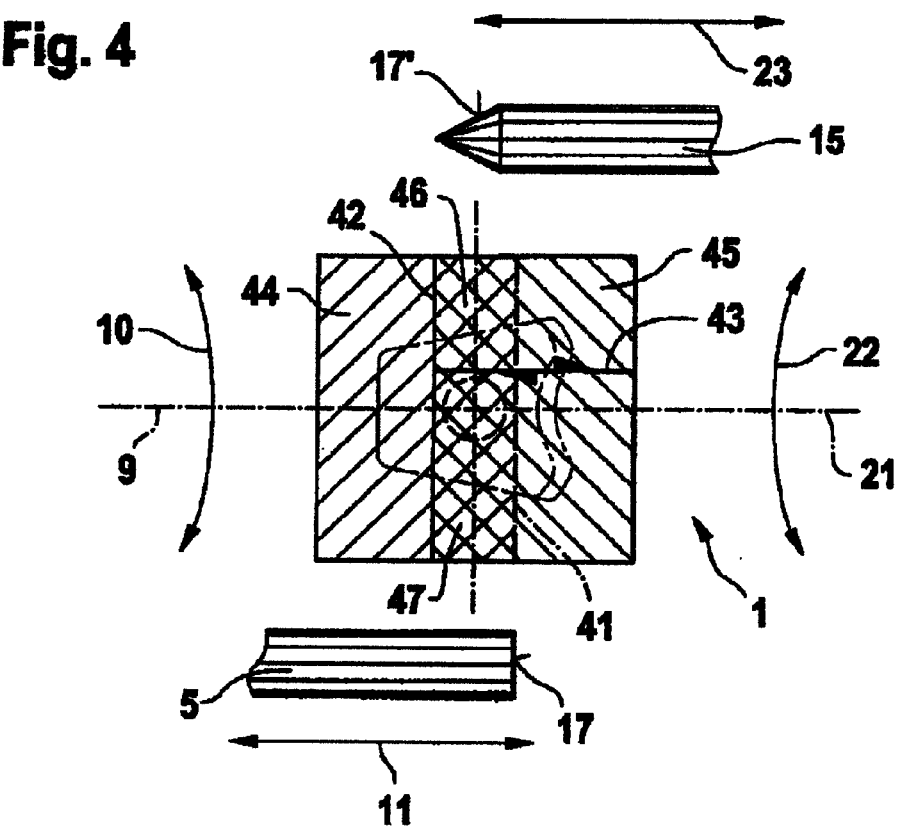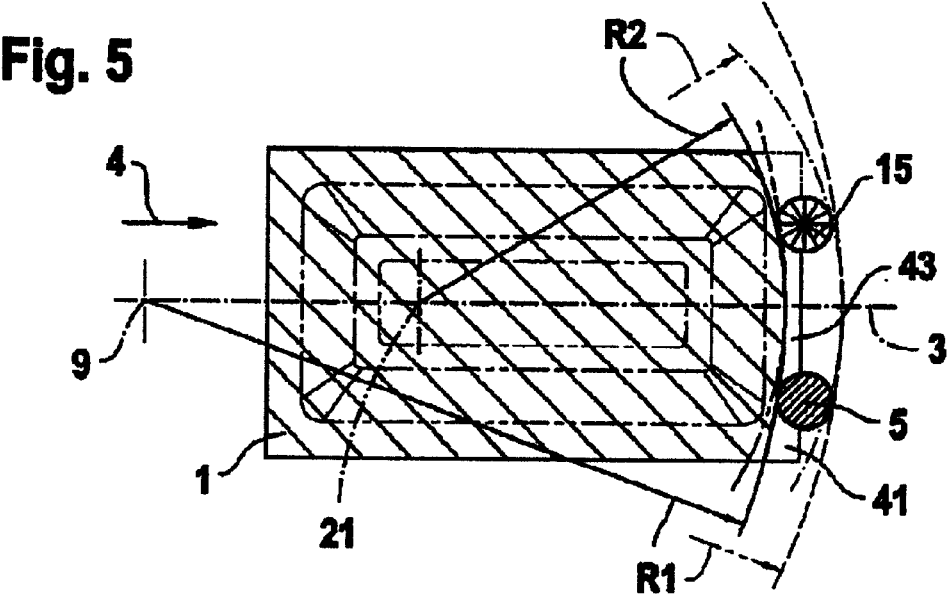

DEVICE AND METHOD FOR PRODUCTION OF MEDICAL FITTINGS

The invention relates to a device and a method for production of medical fittings, in particular dental restorations. Dental restorations are here intended to cover both alloplastic and endoprosthetic/exoprosthetic fittings. In the dental field, these can be inlays, onlays, crowns, bridges, prostheses, implants or veneers.

EP 0,455,853 A1 discloses a device for production of medical, in particular dental, prosthetic fittings, with a receiver for a workpiece from which the fitting is produced. The receiver is connected to a workpiece spindle which is designed in such a way that the workpiece can be moved in the axial direction about a feed axis. For machining the workpiece, a first tool spindle is provided with at least one machining tool which can be set in rotation, the tool spindle being arranged and mounted in such a way that the at least one tool held by it can be moved toward and away from the workpiece perpendicular to the feed axis of the workpiece spindle. Moreover, a second tool spindle is provided which, as regards movement relative to the workpiece, is arranged and mounted in the same way as the first tool spindle, but preferably offset 180° relative to the latter and driven separately. In addition, control means are provided which control the drive mechanisms of the tool receiver and of the tool spindles for simultaneous machining of the workpiece according to predetermined contour data.

By means of the two separately arranged and separately driven spindles for machining tools which can be set in rotation, it is possible to synchronize their movement with the movement of the workpiece and to machine the fitting to be produced practically simultaneously with two tools, as a result of which the work time for production of a fitting can be substantially reduced.

The two spindles lying opposite each other can be arranged in one plane, it being possible to choose between a horizontal arrangement of the spindles or an arrangement in which the spindles are perpendicular to the aforementioned plane or at an angle to it.

The simultaneous machining is carried out with a grinding wheel, driven by one work spindle, shaping the outer contours of the crown, and with an end-milling cutter practically following behind the grinding wheel. The end-milling cutter finishes or smoothes the surface and shapes the fissures which, because of the large radius of the grinding wheel, cannot be shaped by the latter.

The object of the invention is to find a tool combination and a method by which the shapes of medical fittings, particularly of typical dental restorations, can be formed especially quickly and with precision. In this connection, it is to be ensured that the fittings are not destroyed by the machining forces. It is also necessary for the tools to permit a simple construction of the machine. Finally, the tools are intended to permit efficient load control.

This object is achieved by the features of claim 1. According to the invention, the machining tools are designed as rods which can be set in rotation and have radial and terminal working faces. During machining of the workpiece, the machining tools are arranged at approximately the same height relative to the feed axis of the workpiece, so that they work along closely adjacent machining areas.

The fact that the machining tools work at approximately the same height prevents the machining forces from destroying the fitting. Also, because the workpiece is machined at approximately the same height, the machining time is kept short. By using rods which can be set in rotation and have radial and terminal working faces, the final geometries can be obtained in a single operating pass. A second pass is not needed.

The workpiece can preferably be advanced in the axial direction, so that the machining tools do not have to be moved in the axial direction. This permits a simple construction of the machine.

In order to produce height and depth differences in the fitting, it is advantageous if the machining tools can be moved toward and away from the workpiece, along a first machining direction perpendicular to the feed axis of the workpiece.

Moreover, in order to produce a circumferential contour, it is advantageous if the machining tools can be moved along the workpiece along a second machining direction essentially perpendicular to the feed axis of the workpiece and essentially perpendicular to the first machining direction.

To achieve efficient load control, it is advantageous for the first and second machining tools to be driven separately.

In order to coordinate the two machining tools, it is advantageous to provide control means which control the movement of the machining tools for simultaneous machining of the workpiece according to predetermined contour data.

The machining areas advantageously lie essentially perpendicular to the feed axis, which means that it is possible to dispense with additional adjustment mechanisms for the machining tools, since the workpiece is advanced sufficiently and the machining tools do not have to be adjusted in the direction of the feed axis. This does not mean that the machining tools do not move, but that the machining tools are only moved in accordance with a predetermined machining area, which, relative to the device, is always the same.

To avoid machining forces, it is advantageous if the machining areas lie at most one tool diameter from each other.

To permit a precise orientation of the workpiece within the device, it is advantageous if the workpiece can be rotated about the feed axis. Moreover, the formation of undercuts is at least in part possible.

In order to obtain the second machining direction, it is advantageous if the first and/or second machining tool can be moved about an axis of rotation arranged parallel to the tool axis. Alternatively, a linear spindle drive can also be provided, but this is more complicated in constructional terms.

The machining tools are advantageously spaced apart relative to the axis of rotation in such a way that the machining areas touch and/or at least partially overlap.

This can be achieved, for example, by the distances of the two tools from the respective axes of rotation being identical. If the distances are different, the position of the axis of rotation within the device can be changed so that the machining areas touch and/or at least partially overlap.

To produce a typical dental restoration, it is advantageous if one machining tool is a cylinder grinder and the other machining tool is a grinder rod tapering toward a point.

By means of the cylinder grinder, it is possible to sharply define the inner edges of a restoration. The top side of the restoration can be formed using a tapering grinder rod, and fissures can be produced with a high degree of detail and precision if the grinder rod, tapering toward a point, has a point radius of 0.1 to 0.5 mm and a cone angle of 15° to 55°. The control characteristics can also be governed in this way.

To form an undercut on the fitting, it is advantageous if at least one tool can be swiveled about a swivel axis in such a way that the first machining direction of the tool is arranged at an angle of less than 90° relative to the feed axis of the workpiece.

The invention also relates to a method for production of medical fittings, in particular dental restorations, using a machining device with at least two simultaneously operating machining tools, the workpiece, during machining, being guided in the axial direction along a feed axis past the tools. According to the invention, the machining tools are designed as rods which can be set in rotation and have radial and terminal working faces effecting radial and/or terminal removal of material, and the machining tools are guided in closely adjacent machining areas on the workpiece and consequently work at approximately the same height relative to the feed axis.

The advantage of this method lies in the fact that the fittings are not destroyed by machining forces, and the special geometry of the machining tools permits timesaving machining.

Height and depth profiles can be produced by virtue of the fact that the workpiece, during machining, is guided in the axial direction past the tools, and at least one tool is moved toward and away from the workpiece in a first machining direction which is perpendicular to the feed axis of the workpiece.

The method is advantageously carried out with the workpiece being advanced in the axial direction, and the workpiece being rotated about the feed axis to form undercuts.

In order to completely machine the outer surfaces of the fittings, it is advantageous if the machining tools can impinge into the machining area of the other. machining tool.

In order to permit optimum time control of the machining tools, it is advantageous if the machining tools work in opposite directions in the area of the workpiece in which the fitting is produced. To ensure that the machining tools do not touch one another, safety control function is provided which leads to deflection of one of the two machining tools.

In order to form undercuts in the surface of the fitting, at least one machining tool can be swiveled about a swivel axis in such a way that the first machining direction of the tool is arranged at an angle of less than 90° relative to the feed axis of the workpiece.

To avoid collisions of the two machining tools, the movements of the two machining tools are synchronized at the end of each machining area, by each machining tool leaving the trajectory assigned to it and by the faster machining tool waiting for the slower machining tool.

In order to produce a fitting which can be divided into an upper part and a lower part delimited by an equator line, one machining tool advantageously machines the upper part, and the other machining tool machines the opposite lower part of the fitting.

If the aim is to produce all the essential shapes of restorations of this geometry in one operating pass, it is advantageous to use a cylinder grinder for the lower part, and to use a grinder rod, tapering toward a point, to machine the upper part.

A grinding machine for producing dental restorations from a ceramic blank represented in the drawing, and the invention will be explained with reference to this.

Figure 2:
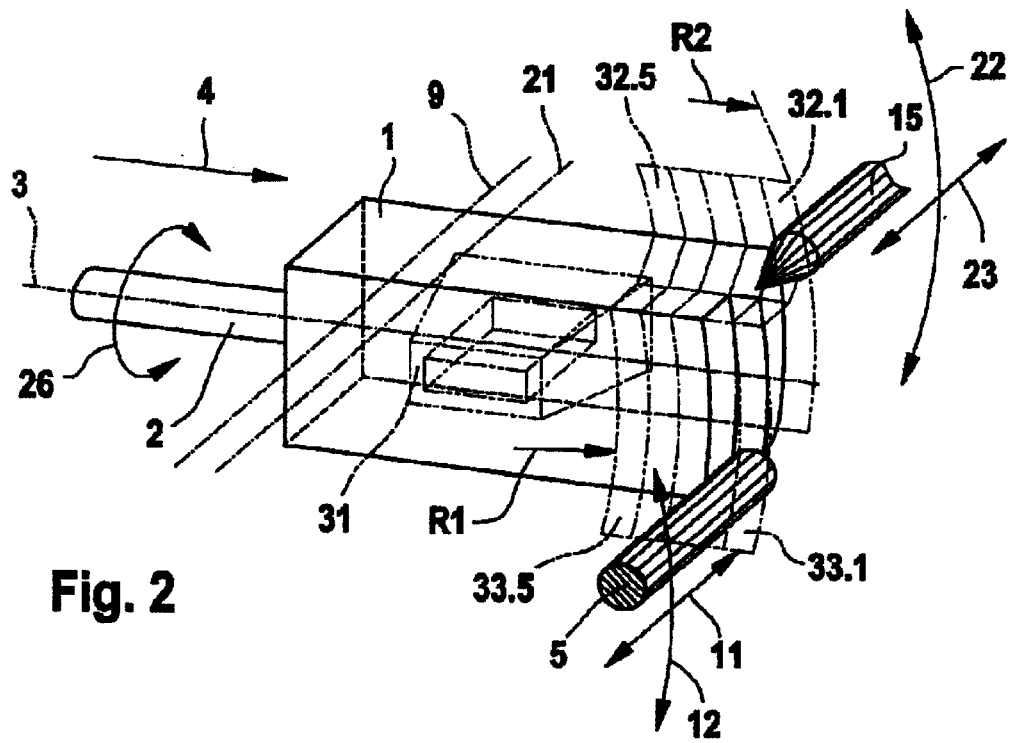
Figure 3:
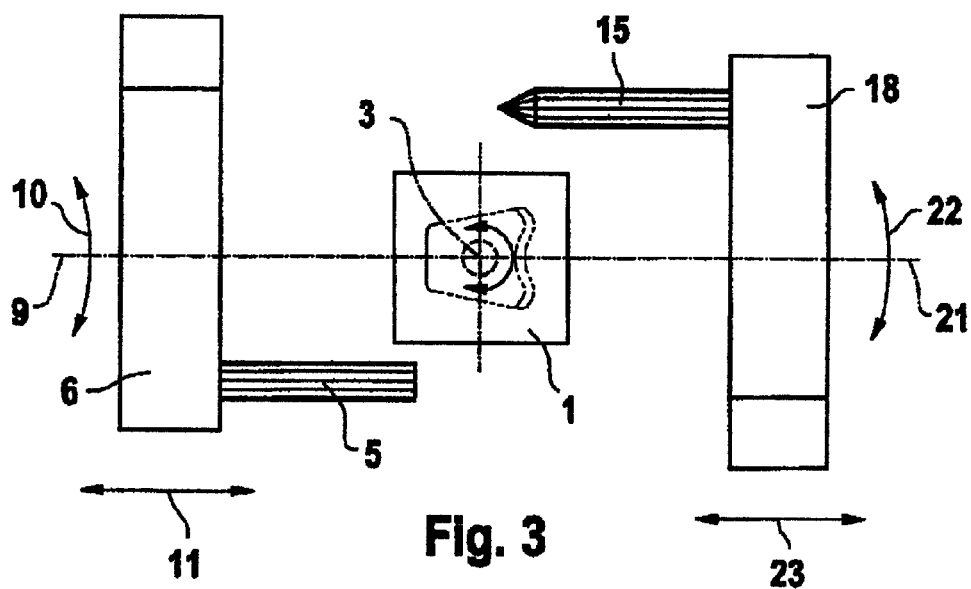
Figure 6:
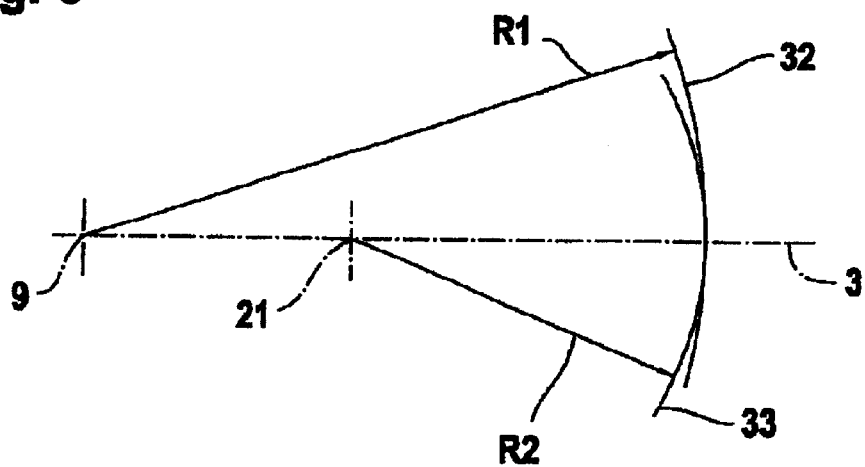

In the drawing:

FIG. 1 shows basic construction of a grinding chamber of a grinding machine,

FIG. 2 shows the position of different machining areas relative to the workpiece which is to be machined, FIG. 3 shows a view of the grinding chamber in the direction the front toward the workpiece, FIG. 4 shows a view of the workpiece from the front according to FIG. 3, on an enlarged scale and showing the grinding trajectories and machining areas, FIG. 5 shows a view of the workpiece from FIG. 3, as seen from the left side in FIG. 3, omitting the tool spindles of the cylinder miller, and FIG. 6 shows the machining areas on the workpiece of an already partially produced fitting.

Figure 7:
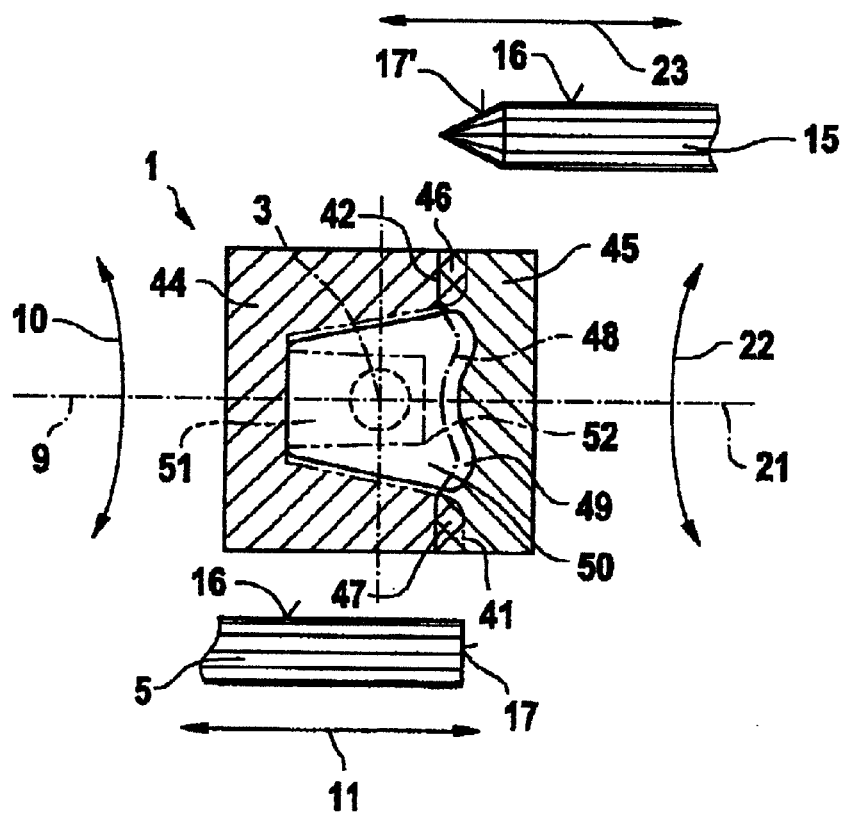

FIG. 7 shows the course of the machining in an area of the workpiece in which the fitting has already been partially prepared from the workpiece.

Part of a grinding chamber in a device according to the invention for production of medical fittings, in particular dental restorations, is shown in FIG. 1. A workpiece 1 is secured via a holder 2 in a workpiece spindle (not shown) and, by means of the workpiece spindle, can be moved in the axial direction along a feed axis 3, as indicated by the arrow 4. Arranged to one side of the feed axis 3, a first machining tool 5 is mounted in a tool spindle 6 and can be set in rotation by means of a motor 7. The machining tool 5 is designed as a cylinder grinder. The machining tool 5 rotates about a tool axis 8. The tool axis 8 is perpendicular to the feed axis 3.

The tool spindle 6 can be moved about an axis of rotation 9, as represented by the arrow 10. The tool spindle 6 can also be moved toward and away from the workpiece 1 along the axis of rotation 9 along a first machining direction, as represented by the arrow 11, perpendicular to the feed axis 3 of the workpiece.

As a result of the possibility of movement about the axis of rotation 9, the machining tool 5 can be moved along the workpiece 1 along a second machining direction, as represented by the arrow 12, essentially perpendicular to the feed axis 3 of the workpiece and essentially perpendicular to the first machining direction 11.

The tool 5 can moreover be swiveled about a swivel axis 13, as represented by the arrow 14, perpendicular to the feed axis 3 and to the axis of rotation 9, as a result of which the first machining direction 11 of the tool 5 can assume an angle of less than 90° relative to the feed axis 3 of the workpiece. By this means, undercuts can be formed on the workpiece 1 with the machining tool 5.

Arranged on the other side of the feed axis 3 is a second machining tool 15 which is designed as a grinder rod with a conical point and a point radius of 0.1to 0.5 mm. The machining tools 5, 15 have radial working faces 16 and terminal working faces 17, and, in the case of the machining tool 5 in the form of a cylinder grinder, the working face 17 is perpendicular to the tool axis 8, so that there is an angle of 90° at the transition from the radial working face to the terminal working face. In the second machining tool 15, the terminal working face is designed as a cone with a cone angle of 15° to 55° , the point having a point radius of 0.1 to 0.5 mm, so that depressions with at least the angle of aperture of twice the cone angle can be produced here.

The second machining tool 15 is mounted in a tool spindle 18 and can be driven by means of a drive mechanism 19 about a second tool axis 20 which is perpendicular to the feed axis 3. The tool spindle 18 can be moved about an axis of rotation 21 which is perpendicular to the feed axis 3 and offset with respect to the tool axis 20 by a distance $R_2$, indicated by the arrow 22. The tool spindle 18, and with it the second machining tool 15, can be moved along the tool axis 20 and the axis of rotation 21 toward the feed axis 3, as indicated by the arrow 23.

Finally, the tool spindle 18 can also be swiveled about a swivel axis 24 perpendicular both to the feed axis 3 and also to the tool axis 8, as represented by the arrow 25, as a result of which undercuts can also be formed with the machining tool 15.

To form three-dimensional undercuts, the workpiece 1 can rotate about the feed axis 3, as represented by the arrow 26.

The tools 5, 15 are represented in a mid position in which the tool axes 8, 20, the axes of rotation 9, 21 and the feed axis 3 all lie in one plane, to which the swivel axis 13, 24 are perpendicular. The machining tools 5, 15 are not in engagement with the workpiece 1.

FIG. 2 shows the workpiece 1, with the fitting 31 to be produced from it, together with the holder. The machining of the workpiece 1 by the machining tools 5, 15 is effected by moving the workpiece 1 along the feed axis 3 in the direction of the arrow 4, as a result of which the workpiece 1 moves past the machining tools 5, 15.

By rotation about the axis of rotation 9, 21 lying perpendciular to the feed axis 3, the machining tools 5, 15 are moved along machining areas 32, 33 oriented almost perpendicular to the feed axis 3 and to the axes of rotation 9, 21. First, that side of the workpiece 1 directed away from the holder 2 is machined along the machining areas 32.1, 33.1. After the machining areas 32.1, 33.1 have been completed, the workpiece 1 is moved along the feed axis 3 in the direction of the arrow 4 by a given distance, at most by the smaller of the two diameters of the machining tools 5, 15. The workpiece 1 is then machined along a new machining area, so that, after it has been advanced five times, the machining area 32.5, 33.5 has been produced.

In FIG. 2, it can be seen that the axes of rotation 9, 21 of the tool spindles do not coincide. However, in order to keep the machining areas 32, 33 at approximately the same height relative to the feed axis 3 of the workpiece, the distances of the axes of rotation 9, 21 from the machining areas 32, 33 are different. In the illustrative embodiment, the distance $R_1$ is greater than the distance $R_2$, the machining areas 32, 33 lying closely adjacent as a result of the difference between the axes of rotation 9, 21.

The arrows 11, 23 also indicate that the machining tools 5, 15 can be moved toward and away from the feed axis 3.

FIG. 3 shows the initial position of the machining tools 5, 15 at the start of a machining operation, looking toward that end of the workpiece 1 remote from the holder, and the fitting which is to be produced is indicated within the workpiece 1. The machining tools 5, 15 have been moved about the axes of rotation 9, 21 so that the work spindle 6 on the left-hand side of the drawing has been moved down relative to the drawing, and the tool spindle 18 on the right-hand side of the drawing has been moved up relative to the drawing. The machining tools 5, 15 are perpendicular to the feed axis 3, which is perpendicular to the plane of the drawing.

To carry out the machining, the machining tools 5, 15 are guided in opposite directions along the workpiece 1 in the directions of the arrows 10, 22, and the machining tools 5, 15 can be moved toward and away from the feed axis 3, and thus toward and away from the workpiece 1, in the direction of the arrows 11, 23.

An illustrative machining path for the two machining tools 5, 15 is represented in FIG. 4. The path of the machining tool 5 is indicated by the dot-and-dash line 41, said line 41 representing the travel of the terminal working face 17. The movement of the machining tool 15 is indicated by the continuous line 42, said line 42 in turn representing the terminal working face 17 of the second machining tool 15. To produce a fitting from the workpiece 1, it is first necessary for material to be removed from the entire surface of the workpiece 1. The material is removed with the machining tool 5 starting at the bottom left in the drawing, while the machining tool 15 starts at the top right in the drawing. The machining tools 5, 15 move in their machining areas (FIG. 2) along the arrows 10, 22 toward one another, the machining tools 5, 15 evading each other in a central area 43. This evasion is achieved by the fact that a collision of the machining tools 5, 15 is set in advance via the control unit, whereupon one machining tool 15 is moved away from the workpiece 1 in the first direction of movement 23, represented by the line 43 with a first section in the direction away from the workpiece and a second section in the direction toward the workpiece, so that the machining tool 5 can be guided unimpeded along the second direction of movement 10 on the workpiece 1. This represents a master-slave type drive of the two machining tools 5, 15, in which the machining tool 15, during its return along the first direction of movement 23, maintains its position relative to the second direction of movement. The machining tool 5 accordingly passes over the machining area 44 which is delimited by the line 41 and which is represented by the hatching from bottom left to top right. The machining tool 15 passes over the machining area 45 which is delimited by the line 42 and which is represented by the hatching from top left to bottom right.

It will be seen from FIG. 4 that, with this control of the machining tools, there are areas 46, 47 within which one machining tool 5, 15 impinges into the machining area of the other machining tool 15, 5.

The geometrical conditions defining the course of the machining areas are once again illustrated in FIG. 5. Starting from the workpiece 1 extending along the feed axis 3, and from which the fitting is to be produced, the machining tools 5, 15 travel along a circular trajectory with radius $R_1$, $R_2$, respectively, and the center points lying on the axes of rotation 9, 21, respectively, along the workpiece 1 in the second machining direction and remove material. No material has been removed in the central area 43, because, as has been explained with reference to FIG. 4, the machining tools 5, 15 will here evade each other in the direction of the second machining direction.

Underneath the machining tool 5 can be seen the course of the line 41, which signifies that the material of the workpiece 1 lying still deeper in the plane of the drawing remains there and is removed at a later point by the machining tool 15. Although the machining tools 5, 15 move on circular trajectories with different radii $R_1$, $R_2$, the machining areas along these circular trajectories are essentially at the same height relative to the feed axis 3 of the workpiece and are essentially perpendicular to the feed axis 3. Instead of a circular movement about the axes of rotation 9, 21, it is of course possible to provide a purely linear movement of the machining tools 5, 15, although this necessitates slightly greater expenditure in terms of equipment. Nevertheless, the teaching of the invention can also be implemented using linearly moved machining tools.

In FIG. 6, the machining areas 32, 33 extending along circular trajectories with radii $R_1$, $R_2$, respectively, are shown diagrammatically. It will be noted that the machining areas 32 and 33 cross into one another in the area of the feed axis 3. If one considers the machining areas as arcs of a circle, then the two arcs touch at the point of intersection with the feed axis 3.

FIG. 7 shows the course of the machining in an area of the workpiece 1 in which the fitting has already been partially prepared from the workpiece 1, so that the machining tools 5, 15 have to produce the contours of the fitting. The dot-and-dash line 41 again indicates the work range of the machining tool 5, said machining tool 5 being moved toward and away from the workpiece in the direction of the arrow 11 and being moved along the workpiece 1 in the direction of the arrow 10. The machining tool 15 is moved toward and away from the workpiece in the direction of the arrow 23 and is moved along the workpiece 1 in the direction of the arrow 22. The machining tools 5, 15 cross each other at an equator line 48 which is created by the series of points of intersection in each machining plane. The equator line 48 divides the fitting into an upper part 49 and a lower part 50, the upper part 49 having been machined exclusively by the machining tool 15, and the lower part 50 having been machined exclusively by the machining tool 5.

The geometries typical of dental restorations mean that it is preferable, for configuration of the lower part 50, to use a cylinder grinder with a terminal working face 17 which is arranged perpendicular to the radial working face 16, so that corners 52 arranged in cavities 51 can be completely worked.

The upper part is configured using a machining tool with a terminal working face 17' in the form of a cone, the cone point having a radius of 0.1 to 0.5 mm. The cone angle, i.e. the angle between the circumferential line of the cone and the tool axis, is between 15° and 55°, so that twice the cone angle, also termed the aperture angle, is between 30° and 110°. Using such grinding geometry, the surface conditions needed to produce dental restorations, and here in particular the fissures, can be made with sufficient fineness. Also, as a result of the conical point, rounded areas can be better approximated to the ideal.

It is not generally necessary to rotate the workpiece 1 about the feed axis 3 in order to produce the fissures. During the entire machining operation, the workpiece 1 can remain in the initially assumed position and is moved only in the direction of the feed axis 3.

At this machining stage too, the machining areas 44, 45 overlap in the areas 46, 47 and one machining tool impinges into the machining area of the other machining tool.

The machining tools 5, 15 are controlled in such a way that, at the end of each machining area, the faster machining tool waits for the slower machining tool before the next machining area is machined.

What is claimed is:

1. A device for production of medical fittings with a workpiece movable in an axial direction along a feed axis, with a first machining tool on one side of the feed axis, and with a second machining tool operating simultaneously on the other side of the workpiece, wherein the machining tool are designed as rods which can be set in rotation and have radial and terminal working faces, and wherein the machining tools, during machining of the workpiece, are arranged at approximately the same height relative to the feed axis of the workpiece, so that they work along closely adjacent machining areas.

2. The device as claimed in claim 1, wherein the workpiece is movable in an axial direction.

3. The device as claimed in claim 1 or 2, wherein the machining tools are movable toward and away from the workpiece along a first machining direction perpendicular to the feed axis of the workpiece.

4. The device as claimed in claim 3, wherein the machining tools are movable along the workpiece along a second machining direction substantially perpendicular to the feed axis of the workpiece and substantially perpendicular to the first machining direction.

5. The device as claimed in claim 1, wherein the first and second machining tools are driven separately.

6. The device as claimed in claim 1, wherein control means are provided which control the movement of the machining tools for simultaneous machining of the workpiece according to predetermined contour data.

7. The device as claimed in claim 1, wherein the machining areas are essentially perpendicular to the feed axis.

8. The device as claimed in claim 1, wherein the machining areas lie at most one tool diameter from each other.

9. The device as claimed in claim 1, wherein the workpiece can be rotated about the feed axis.

10. The device as claimed in claim 1, wherein the first and/or second machining tools can be moved about an axis of rotation arranged parallel to the tool axis.

11. The device as claimed in claim 10, wherein the machining tools are spaced apart relative to the axis of rotation in such a way that the machining areas touch and/or at least partially overlap.

12. The device as claimed in claim 10 or 11, wherein the distances of the two tools from the respective axes of rotation are identical.

13. The device as claimed in claim 1, wherein the machining tool is a cylinder grinder and the other machining tools is a grinder rod tapering toward a point.

14. The device as claimed in claim 13, wherein the grinder rod, tapering toward a point, has a point radius of 0.1 to 0.5 mm and a cone angle of 15° to 55°.

15. The device as claimed in claim 1, wherein at least one tool can be swiveled about a swivel axis in such a way that the fist machining direction of the tool is arranged at an angle of less than 90° relative to the feed axis of the workpiece.

16. A method for production of medical fittings using a machining device with at least two simultaneously operating machining tools, the workpiece, during machining, being guided in the axial direction along a feed axis past the tools arranged to either side of the workpiece, wherein the machining tools are designed as rotatable rods and have radial and terminal working faces effecting one of radial and terminal removal of material, and wherein the machining tools are guided in closely adjacent machining areas on the workpiece and consequently work at approximately the same height relative to the feed axis.

17. The method as claimed in claim 16, wherein the workpiece, during machining, is guided in the axial direction past the tools, and wherein at least one tool is moved toward and away from the workpiece in a first machining direction which is perpendicular to the feed axis of the workpiece.

18. The method as claimed in claim 16 or 17, wherein at least one machining tools is movable along the workpiece along a second machining direction substantially perpendicular to the feed axis of the workpiece and substantially perpendicular to the first machining direction.

19. The method as claimed in claim 16, wherein the workpiece is advanced in the axial direction, and wherein the workpiece is rotated about the feed axis to form undercuts.

20. The method as claimed in claim 16, wherein one machining tool impinges at least intermittently into the machining area of the other machining tool.

21. The method as claimed in claim 20, wherein the machining tools work in opposite directions in the area of the workpiece in which the fitting is produced.

22. The method as claimed in claim 16, wherein in order to form undercuts in the surface of the fitting, at least one machining tool can be swiveled about a swivel axis in such a way that the fist machining direction of the tool is arranged at an angle of less than 90° relative to the feed axis of the workpiece.

23. The method as claimed in claim 16, wherein the movements of the two machining tools are synchronized at the end of each machining area, by each machining tool leaving the trajectory assigned to it and by the faster machining tool waiting for the slower machining tool.

24. The method as claimed in claim 16, wherein the fitting to be produced can be divided into an upper part and a lower part delimited by an equator line, one machining tool machining the upper part, and the other machining tool machining the opposite lower part of the fitting.

25. The method as claimed in claim 16, wherein a cylinder grinder is used to machine the lower part, and a grinder rod tapering toward a point is used to machine the upper part.

26. A method for production of medical fittings using a machining device with at least two simultaneously operating machining tools, the workpiece, during machining, being guided in the axial direction along a feed axis past the tools arranged to either side of the workpiece, wherein the machining tools are designed as rotatable rods and have radial and terminal working faces effecting radial and terminal removal of material, and wherein the machining tools are guided in closely adjacent machining areas on the workpiece and consequently work at approximately the same height relative to the feed axis.

27. The method as claimed in claim 26, wherein the workpiece, during machining, is guided in the axial direction past the tools, and wherein at least one tool is moved toward and away from the workpiece in a first machining direction which is perpendicular to the feed axis of the workpiece.

28. The method as claimed in claim 26 or 27, wherein at least one machining tools is movable along the workpiece along a second machining direction substantially perpendicular to the feed axis of the workpiece and substantially perpendicular to the first machining direction.

29. The method as claimed in claim 26, wherein the workpiece is advanced in the axial direction, and wherein the workpiece is rotated about the feed axis to form undercuts.

30. The method as claimed in claim 26, wherein one machining tool impinges at least intermittently into the machining area of the other machining tool.

31. The method as claimed in claim 30, wherein the machining tools work in opposite directions in the area of the workpiece in which the fitting is produced.

32. The method as claimed in claim 26, wherein in order to form undercuts in the surface of the fitting, at least one machining tool can be swiveled about a swivel axis in such a way that the fist machining direction of the tool is arranged at an angle of less than 90° relative to the feed axis of the workpiece.

33. The method as claimed in claim 26, wherein the movements of the two machining tools are synchronized at the end of each machining area, by each machining tool leaving the trajectory assigned to it and by the faster machining tool waiting for the slower machining tool.

34. The method as claimed in claim 26, wherein the fitting to be produced can be divided into an upper part and a lower part delimited by an equator line, one machining tool machining the upper part, and the other machining tool machining the opposite lower part of the fitting.

35. The method as claimed in claim 26, wherein a cylinder grinder is used to machine the lower part, and a grinder rod tapering toward a point is used to machine the upper part.

* * * * *